(12) United States Patent
Ito et al.

(10) Patent No.: US 6,607,710 B1
(45) Date of Patent: Aug. 19, 2003

(54) BISPHOSPHONIC ACID DERIVATIVE AND COMPOUND THEREOF LABELED WITH RADIOACTIVE NUCLIDE

(75) Inventors: Osamu Ito, Sodegaura (JP); Nobuhiko Kanazashi, Sodegaura (JP); Aki Morishita, Sodegaura (JP); Masamichi Hara, Sodegaura (JP); Masaru Kanagawa, Sodegaura (JP); Yasuko Watanabe, Sodegaura (JP); Yoshitoshi Itaya, Sodegaura (JP)

(73) Assignee: Nihon Medi-Physics Co., Ltd., Hyogo-ken (JP)

( * ) Notice: Subject to any disclaimer, the term of this patent is extended or adjusted under 35 U.S.C. 154(b) by 5 days.

(21) Appl. No.: 09/686,372

(22) Filed: Oct. 12, 2000

(30) Foreign Application Priority Data

Oct. 12, 1999 (JP) ............................................. 11-288952

(51) Int. Cl.⁷ ........................ A61K 51/00; A61M 36/14
(52) U.S. Cl. ..................... 424/1.77; 424/1.11; 424/1.65; 424/9.1
(58) Field of Search ................................ 424/1.11, 1.65, 424/1.77, 9.1

(56) References Cited

U.S. PATENT DOCUMENTS

| 4,693,884 A | 9/1987 | Kleiner et al. |
| 6,080,785 A | 6/2000 | Platzek et al. |

FOREIGN PATENT DOCUMENTS

| DE | 36 33 243 A | 3/1988 |
| GB | 1 435 295 A | 5/1976 |
| WO | WO 87 01289 A | 3/1987 |
| WO | WO 89 11877 A | 12/1989 |
| WO | WO 97 25305 A | 7/1997 |

Primary Examiner—Dameron Jones
(74) Attorney, Agent, or Firm—Sughrue Mion, PLLC

(57) ABSTRACT

An object of the present invention is to provide a bisphosphonic acid derivative and said bisphosphonic acid derivative being labeled with a radioactive nuclide, which has properties of rapid accumulation to the bone and rapid urinary excretion. The present invention relates to a bisphosphonic acid derivative and said bisphosphonic acid derivative being labeled with a radioactive nuclide, which is represented by the following general formula (1), $$R-Y-A \tag{1}$$

wherein A is a bisphosphonic acid or a salt thereof, having P—C—P bond; Y is a bonding portion such as a methylene, an amido etc.; R is a group of any one of a polyaminopolycarboxylic acid, an aliphatic carboxylic acid, a mercaptoacetylpolyamino acid or its derivatives and a compound represented by the formula (2),

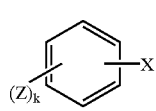

(2)

X is a halogen atom or an isotope thereof or an alkyl tin; Z is a group of any one of compounds of an aminocarboxylic acid, an alkylcarboxylic acid or a substituted-alkylcarboxylic acid, an alkylsulfonic acid or a substituted-alkylsulfonic acid.

24 Claims, No Drawings

BISPHOSPHONIC ACID DERIVATIVE AND COMPOUND THEREOF LABELED WITH RADIOACTIVE NUCLIDE

BACKGROUND OF THE INVENTION

1. Field of the Invention

The present invention relates to a bisphosphonic acid derivative having an affinity to the bone, the bisphosphonic acid derivative labeled with a radioactive nuclide, a method for labeling the bisphosphonic acid derivative with the radioactive nuclide, and a radioactive agent for diagnosis or therapy of bone disease, containing the bisphosphonic acid derivative labeled with the radioactive nuclide as the active ingredient.

2. Related Art

In recent years, a scintigraphy of the skeleton in methods of nuclear medicine becomes one of the important test methods in its early stage for diagnosis of the bone disease. As to an imaging agent used for scintigraphy of the bone, said agent requires shorten intervals between the administration of the imaging agent and the timing of taking a scintigram, further such agent should have the properties of high affinity to the bone and of efficient urinary excretion, as well as rapid clearances from the blood and non-osseous tissues.

At present, a phosphonic acid derivative labeled with a radioactive isotope may be used for the above-mentioned purposes, and an inorganic polyphosphonic acid labeled with 99m-Technetium was used as the first example therefor. However, such inorganic polyphosphonic acids labeled with 99m-Technetium perform inevitably the lower clearance from the blood, because such compounds may be changed to the corresponding monophosphates by hydrolysis in aqueous solutions.

In order to solve such problems, Yano, et al. reported stannous Tc-99m-ethane-1-hydroxy-1,1-diphosphonate (Tc-99m-HEDP), which is an organic diphosphonic acid labeled with 99m-Technetium [J. Nucl. Med., 14, 73, (1973) and U.S. Pat. No. 3,735,001)]. By use of said compound, the bone scintigraphy can be carried out in the earlier stage of test after the compound is administered, because this compound has property of relatively rapid clearance from the blood. For this reason, compounds of phosphonic acid labeled with 99m-Technetium, which are compounds similar to Tc-99m-HEDP, for example compounds relating to organic diphosphonic acid, such as methanediphosphonic acid (MDP), 3,3-diphosphono-1,2-propanedicarboxylic acid (DPD) and hydroxymethanediphosphonic acid (HMDP) and the like, being labeled with 99m-Technetium are widely used for this purpose. These compounds are used for pharmaceutical preparations for bone scintigraphy, which can deposit or accumulate to the sites where calcification of the bone is taken place, and such compounds make an interval between the administration of the imaging agent and the timing of taking a scintigram shorten. However, these compounds are still not good enough in connection with the waiting time, because they require waiting time for about 3 hours after the administration of compound to take a scintigram.

Generally, in conducting a bone scintigraphy, when the radioactivity of imaging agent disappears slowly from the blood and/or soft tissue with the slower urinary excretion, then a certain length of time for lowering the background of radioactivity is required, and it is necessary to have the longer waiting time for taking a scintigram after the administration of imaging agent. When a phosphonic acid compound labeled with Technetium is used, the polymer structure thereof may be considered as one of the factors for giving influence on the clearance. The phosphonic acid compound labeled with Technetium may give high possibility of affecting the clearance due to the formation of polymer structure. Attempt at realizing the rapid clearance in the earlier stage after the administration of an imaging agent by changing the polymer structure of the radiolabeled bisphosphonic acid compound to monomolecular structure has been made with a bisphosphonate compound labeled with 123-Iodine (WO 89/11877), but satisfactory result has not been obtained yet. When a possible coordination site for a radioactive metal, other than the phosphonic acid group, is introduced to a bisphosphonate compound, the compound labeled with a radioactive metal might give a stable monomolecular structure. However, such trial described above with available compounds for use in bone scintigraphy has not been carried out and, of course, properties of the resultant monomolecular compound as a bone imaging agent have not been examined.

Under the circumstances, an object of the present invention is to provide a bisphosphonic acid derivative having the properties of rapid accumulation to the bone and rapid urinary excretion, and a compound thereof labeled with a radioactive nuclide.

SUMMARY OF THE INVENTION

The present invention provides a bisphosphonic acid derivative or salt thereof represented by the following formula (1):

$$R\text{—}Y\text{—}A \tag{1}$$

wherein A is a bisphosphonic acid or salt thereof, having a P—C—P bond; Y is a bonding portion selected from the group consisting of —(CH$_2$),—, —[(CH$_2$)$_m$(NHCO)$_r$(CH$_2$)$_n$]$_q$—, —[(CH$_2$)$_m$(CONH)$_r$(CH$_2$)$_n$]$_q$— and —(CH$_2$)$_o$—S—(CH$_2$)$_p$—; k, l, m, n, o, p, q, and r are each represents independently an integer, and k=0 or 1; l=0 to 6; m=0 to 6; n=1 to 6; o=0 to 6, p=0 to 6; q=1 to 6; and r=1 to 6; R is a group of any one of compounds selected from the group consisting of a polyaminopolycarboxylic acid, an aliphatic carboxylic acid, a mercaptoacetylpolyamino acid or its derivative and a compound represented by the following formula (2),

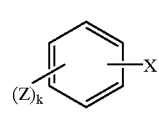

(2)

and in the formula (2), X is a halogen atom or its isotope, or alkyl tin; Z is a group of any one of compounds selected from the group consisting of an aminocarboxylic acid, an alkylcarboxylic acid, a substituted-alkylcarboxylic acid, an alkylsulfonic acid and a substituted-alkyl sulfonic acid.

A radiolabeled bisphosphonic acid derivative prepared by labeling the above-mentioned bisphosphonic acid derivative with a radioactive nuclide is useful as an active ingredient of radiopharmaceutical for the bone scintigraphy or the bone disease therapy, and as to preferable radioactive nuclides, 99m-Technetium, 111-Indium, 117m-Tin, 153-Samarium, 186-Rhenium, 188-Rhenium, 123-Iodine, 125-Iodine, 131-Iodine, 211-Astatine and the like can be exemplified.

The above-mentioned bisphosphonic acid derivative labeled with radioactive nuclide represented by the formula (1), wherein R is a group being labeled with radioactive halogen or a radioactive transition metal; and A is a free form of bisphosphonic acid or salt thereof without participating in the formation of complex with said radioactive transition metal or other metal, is one of the embodiments of the present invention and is useful as the active ingredient of a radiopharmaceutical for the bone scintigraphy or the bone disease therapy.

Another embodiment of the present invention is, in case of labeling the bisphosphonic acid derivative with a radioactive transition metal, a labeling method that a bisphosphonic acid derivative is allowed to react with a peracid ion of radioactive transition metal in the presence of non-metallic reducing agent to form a complex.

Preferably, said peracid ion of the radio-active transition metal is selected from any one of the group consisting of pertechnetate (Tc-99m), perrhenate (Re-186), and perrhenate (Re-188); and the non-metallic reducing agent is selected from any one of the group consisting of sodium diphenylphosphinobenzene-3-sulfonate, formamidine-sulfonic acid and glucoheptanoic acid.

DETAILED DESCRIPTION OF THE INVENTION

The present invention provides, as represented by the above-mentioned formula (1), a bisphosphonic acid derivative wherein a bisphosphonic acid having the affinity to the bone is combined with a group capable of being labeled with a radioactive transition metal or a radioactive halogen. The bisphosphonic acid derivative having the affinity to the bone can be used as the active ingredient of agent for diagnosis or therapy of bone disease by radiolabeling.

In the formula (1), A is alpha-geminal-bisphosphonic acid, i.e., bisphosphonic acid having P—C—P bond, or its derivative. To the alpha-carbon atom, bonding group exemplified by Y is attached and an atom or a group selected from the group consisting of a hydrogen atom, a hydroxyl group, an amino group, a halogen atom, a carboxylic acid group, a sulfonic acid group, a lower alkyl group, a lower alkylalcohol group and a cyano group may be also attached to the alpha-carbon. Methanediphosphonic acid (MDP), hydroxymethane-diphosphonic acid (HMDP), 1-hydroxyethane-1,1-bisphosphonic acid (EHDP), dimethylaminomethylene-diphosphonic acid (DMAD), 3,3-diphosphono-1,2-propanedicarboxylic acid (DPD) and salts thereof are exemplified as alpha-geminal-bisphosphonic acid without being substituted with group Y.

In the formula (2) as one of the groups of R, the aminocarboxylic acid indicated as symbol Z can be exemplified as glycine, alanine, asparagic acid, glutamic acid, etc.; the alkyl group as indicated in the alkylcarboxylic acid, substituted alkylcarboxylic acid, alkylsulfonic acid, and substituted alkylsulfonic acid can be exemplified as methyl group, ethyl group, propyl group, isopropyl group, n-butyl group, sec-butyl group, tert-butyl group, hexyl group, cyclohexyl group, pentadecanyl group, hexadecanyl group, etc. As to the substituted alkyl group, hydroxyalkyl group, halogenated alkyl group, cyanoalkyl group, etc. can be exemplified.

The symbol X in the formula (2) is a hologen atom or isotopes thereof, and exemplified as iodine, chlorine, bromine, fluorine, astatine, etc., and radioactive isotopes thereof. Among them, 123-Iodine, 125-Iodine, 131-Iodine may be used preferably. Further, X, as a precursor, may be substituted by a halogen atom or trialkyl tin, and a substitute group which can be easily substituted by a halogen atom or its isotope may be used, and bromine, trimethyl tin, tributyl tin etc. may be exemplified. The bonding positions of X and Z as the substituents in the phenyl group are not specifically restricted, preferably X is bonded at ortho-position or meta-position to the position of Z.

As to the polyaminopolycarboxylic acid, for example, ethylenediaminetetraacetic acid (EDTA), diethylenetriaminepentaacetic acid (DTPA), triethylenetetraminehexaacetic acid (TTHA), and hydroxyethylenediaminetriacetic acid (HEDTA) may be used.

As to the aliphatic carboxylic acid, alkylcarboxylic acid, substituted alkylcarboxylic acid, etc. may be exemplified, and as to the alkyl group, methyl group, ethyl group, propyl group, isopropyl group, n-butyl group, sec-butyl group, tert-butyl group, hexyl group, cyclohexyl group, pentadecanyl group, hexadecanyl group, etc. can be exemplified. As to the substituted alkyl group, hydroxyalkyl group, halogenated alkyl group, cyanoalkyl group, etc. may be exemplified.

As to the amino acid in mercaptoacetylpolyamino acid, glycine, alanine, threonine, leucine, isoleucine, phenylalanine, valine, methionine, aspargic acid, glutamic acid, serine, tyrosine, asparagine, glutamine, etc. can be exemplified. These amino acids may be arranged repeatedly or at random, and among them, mercaptoacetylglycylglycylglycine may be used preferably.

As to embodiments of the bisphosphonic acid derivative represented by the formula (1), compounds represented by the following formulas (3) to (12) may be exemplified.

As to an example of introducing a functional group, accelerating urinary excretion, into bisphosphonic acid, there is a bio-adduct type compound being bonded bisphosphonic acid with the amino group in amino acid, and in the formula (1), when R is carboxyl group, the compound may be shown by the following formula (3):

HOOC—Y—A (3)

Specifically, in case of single lower molecular weight amino acid having carboxylic acid, it is preferably to bond bisphosphonic acid thereto, for example, as shown in the formula (4), glycine adduct compound of N-(3,3-diphosphonopropionyl)glycine can be exemplified, wherein the glycine adduct compound has both carboxylic acid group and bisphosphonic acid group:

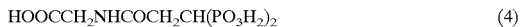

HOOCCH$_2$NHCOCH$_2$CH(PO$_3$H$_2$)$_2$ (4)

As to amino acids other than the glycine, there can be exemplified alanine, threonine, leucine, isoleucine, phenylalanine, valine, methionine, asparaginic acid, glutaminic acid, serine, tyrosine, asparagine, glutamine, etc. and these amino acids can be arranged repeatedly or at random.

The following formula (5) shows bisphosphonic acid derivative of a monomolecular structure type, which does not form polymer structure, wherein R in the above-mentioned formula (1) is the formula (2). There can be mentioned bisphosphonic acid derivative prepared by substituting an aromatic carboxylic acid or an aromatic aminocarboxylic acid with bisphosphonic acid, or by introducing bisphosphonic acid into the aromatic ring.

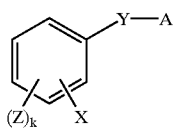
(5)

For example, as shown in the following formula (6), 2-(2-iodobenzamido)-1,1-diphosphonoethane prepared by substituting the carboxylic acid in hippuric acid with bisphosphonic acid, which can be easily labeled with radioactive iodine and having excellent affinity to the bone and the property of efficient urinary excretion.

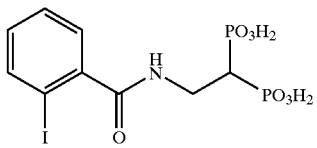
(6)

Further, as shown in the following formula (7), 2-iodo-4-(4,4-diphosphonopropionamido)hippuric acid prepared by introducing bisphosphonic acid into the phenyl group and remaining the structure of glycine carboxylic acid in hippuric acid, can be easily labeled with radioactive iodine and has the property of being rapidly excreted into urine, thus, said compound is useful as a carrier or a precursor for agent for diagnosis or therapy of the bone disease.

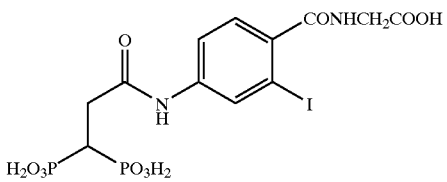
(7)

As shown in the following formulas (8) and (11), those bisphosphonic acid derivatives are functional group type derivatives prepared by introducing bisphosphonic acid into the metallic coordinating functional group which can form complex with a radioactive metal such as 99m-Technetium suitable for scintigraphy, or 186-Rhenium, 188-Rhenium effective as an in vivo a radiation source for bone disease therapy. As to the metallic coordinating functional group, the above-mentioned polyaminopolycarboxylic acid, mercaptoacetylpolyamino acid, etc. can be used. As to these examples, any compounds capable to form complex with a metal can be selected, such as diethylenetriaminepentaacetic acid (DTPA), ethylene cysteine dimer diethyl ester (ECD), 1,4,7,10-tetraazacyclododecane-N,N', N",N'"-tetraacetic acid (DOTA), 1,4,7,10-tetraazacyclododecane-1,4,7,10-α,α',α",α'"-tetrakis (methylacetic acid) (DOTMA), 1,4,8,11-tetraazacyclododecane-N,N',N",N'"-tetraacetic acid (TETA), mercaptoacetylglycylglycylglycine (MAG3). Among them, DTPA may be preferably used. Further, the bonding position of the metallic coordinating functional group with bisphosphonic acid may be any position and can be selected suitably.

Formula (8) shows a compound represented by formula (1) wherein R is a polyaminopolycarboxylic acid and said carboxyl group is substituted by $R^1$ or $R^2$.

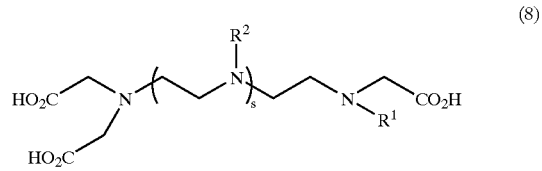
(8)

In formula (8), Y and A are defined previously in formula (1), $R^1$ and $R^2$ are each represents Y—A or Y—COOH, and when s=0, then $R^1$ is Y—A; when s=1 and $R^1$ is Y—A, then $R^2$ is Y—COOH, when $R^1$ is Y—COOH, then $R^2$ is Y—A; when s=2 to 4 and $R^1$ is Y—A, then $R^2$ is Y—COOH; and when $R^1$ is Y—COOH, then one of $R^2$ is Y—A and another $R^2$ is Y—COOH.

As to specific example of the bisphosphonic acid derivatives, wherein the carboxyl group of polyaminopolycarboxylic acid is substituted by bisphosphonic acid, 3,6-bis(carboxymethyl)-9-(((2,2-diphosphonoethyl)carbamoyl) methyl)-3,6,9-triazaundecanedicarboxylic acid is shown in formula (9),

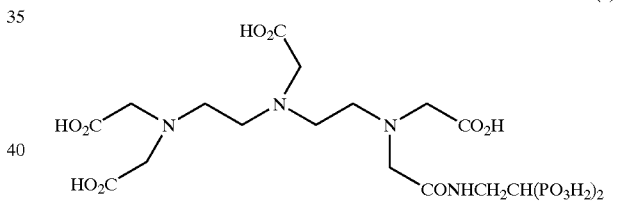
(9)

and 3,6-bis(carboxylmethyl)-6-(((2,2-diphosphonoethyl) carbamoyl)methyl)-3,6,9-triazaundecanedicarboxylic acid is shown in formula (10).

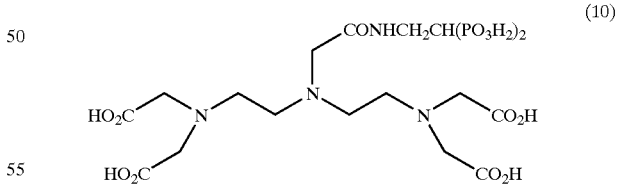
(10)

Bisphosphonic acid derivative as shown in formula (11) is a compound wherein R in formula (1) is mercaptoacetylpolyamino acid. In formula (11), Y and A are each defined previously in formula (1), $R^3$, $R^4$, $R^5$ and $R^6$ are respectively Y—A or a hydrogen atom; and when $R^3$ is Y—A, then $R^4$, $R^5$ and $R^6$ are hydrogen atoms; when $R^4$ is Y—A, then $R^3$, $R^5$ and $R^6$ are hydrogen atoms; when $R^5$ is Y—A, then $R^3$, $R^4$ and $R^6$ are hydrogen atoms; and when $R^6$ is Y—A, then $R^3$, $R^4$ and $R^5$ are hydrogen atoms.

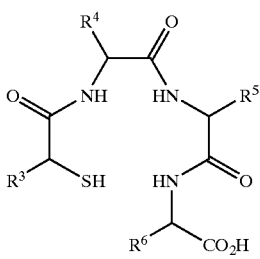

(11)

As to preferable bisphosphonic acid derivative, N-mercaptoacetyl-2-[4-(4,4-diphosphonopropioneamide)butyl]glycylglycylglycine is exemplified as the formula (12).

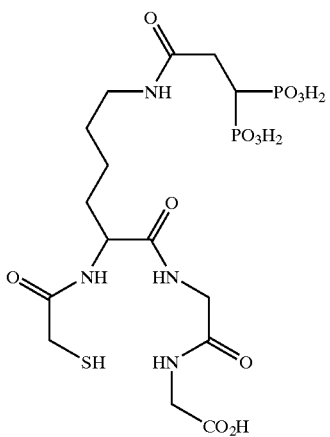

(12)

As to the radioactive nuclide to be used for radiolabeling the above-mentioned bisphosphonic acid derivatives or salts thereof, in accordance with applications, i.e., in vivo radioactive diagnostic imaging or in vivo radiotherapy, it is selected from the group consisting of 11-Carbon ($^{11}C$), 15-Oxygen ($^{15}O$), 18-Fluorine ($^{18}F$), 32-Phosphorus ($^{32}P$), 52-Iron ($^{52}Fe$), 59-Iron ($^{59}Fe$), 62-Zinc ($^{62}Zn$), 64-Copper ($^{64}Cu$), 67-Copper ($^{67}Cu$), 67-Gallium ($^{67}Ga$), 81m-Krypton ($^{81m}Kr$), 81-Rubidium (8Rb), 87m-Strontium ($^{87m}Sr$), 89-Strontium ($^{89}Sr$), 90-Yttrium ($^{90}Y$), 99m-Technetium ($^{99m}Tc$), 111-Indium ($^{111}In$), 115m-Indium ($^{115m}In$), 123-Iodine ($^{123}I$), 125-Iodine ($^{125}I$), 131-Iodine ($^{131}I$), 133-Xenon ($^{133}Xe$), 117m-Tin ($^{117m}Sn$), 153-Samarium ($^{153}Sm$), 186-Rhenium ($^{16}Re$), 188-Rhenium ($^{188}Re$), 201-Thallium ($^{202}Tl$), 212-Bismuth ($^{212}Bi$), 213-Bismuth ($^{213}Bi$) and 211-Astatine ($^{211}At$). As to the nuclide for diagnostic imaging, 99m-Technetium, 111-Indium, 123-Iodine, etc. are preferably used, and as to the nuclide for radiotherapy, 117m-Tin, 153-Samarium, 186-Rhenium, 188-Rhenium, 125-Iodine, 131-Iodine, 211-Astatine, etc. are preferably used.

In the above-mentioned formula (1), the symbol Y is the bonding portion selected from any one of —$(CH_2)_l$—, —$[(CH_2)_m(NHCO)_r(CH_2)_n]_q$—, —$[(CH_2)_m(CONH)_r(CH_2)_n]_q$—, or —$(CH_2)_o$—S—$(CH_2)_p$—, and k, l, m, n, o, p, q, r, are independently to each other, and are preferably selected from integers of k=0 or 1, l=0 to 6, m=0 to 6, n=1 to 6, o=0 to 6, p=0 to 6, q=1 to 6, r=1 to 6.

The salts of compounds of the present invention, are pharmaceutically acceptable salts of inorganic bases, for example salts of alkaline metal, such as lithium, sodium, potassium, etc.; salts of alkaline earth metal, such as calcium, magnesium, etc.; ammonium salt; salts of organic bases for example salts of methylamine, ethylamine, dimethylamine, diethylamine, trimethylamine, triethylamine, cyclohexylamine, ethanolamine, diethanolamine, morpholine, meglumine, etc; salts of basic amino acids for example salt of lysine, ornithine, arginine, etc. can be exemplified. Among them, sodium or potassium is used preferably, and particularly, a mixture of disodium salt with trisodium salt is preferable.

In the present invention, one embodiment of the bisphosphonic acid derivative labeled with radioactive nuclide is a radiolabeled compound which is prepared by labeling a compound represented by the formula (1) with radioactive nuclide, wherein R is a group labeled with radiohalogen or a radioactive transition metal; and A is a bisphosphonic acid of free form or salt thereof which does not participate in radiolabeling.

Japanese patent application Kohyo No. Hei 10-501218 discloses mono-, di- and polyphosphonate complexes labeled with 99m-Technetium, each of which has different composition in accordance with different preparation conditions such as heating in autoclave, heating by microwave, etc. This method is an attempt to improve the slow clearance of an radiotherapentic agent for bone disease due to the formation of polymer structure during the radiolabeling procedure. However, formation of radio metal complex of phosphonates having polymer structure is inevitable by such a method. In consideration of these circumustances, the present invention provides a bisphosphonic acid derivative labeled with a radioactive nuclide as a basic affinity material to the bone, and having the property of advantageously accumulating to the bone, by the formation of radiolabeled bisphosphonic acid derivative wherein the bisphosphonate part does not participate in the complex formation. Thus, one feature of the present invention is a radiohalogenated monomolecular bisphosphonic acid derivative of which bisphosphonate part remains the free form and retain the affinity to the bone like free bisphosphonate. Another feature is a radiolabeled monomolecular bisphosphonic acid derivative retaining the affinity to the bone, in which the bisphosphonate part does not participate in complex formation with a radioactive metal. This feature can be obtained when the complex forming ability of metal coordinating functional group of the bisphosphonic acid derivative is greater than that of bisphosphonate part. The difference of complex forming ability between the metal coordinating functional group and the bisphosphonate part can be proven by use of a related compound of the present invention. Thus, the fact that bisphosphonic acid does not participate in the complex formation can be proven by selecting conditions of labeling such as radioactive metal nuclides, concentrations, pH, reducing agents, etc. In the following Examples, co-existing labeling methods by use of DTPA or MAG3 with HMDP are mentioned. However, the all Examples are disclosing as examples only, and the present invention is not restricted only to the Examples.

By subjecting to labeling with a suitable radioactive nuclide, the compound of the present invention is useful as the active ingredient of a diagnostic agent for bone disease such as bone metastasis, osteoporosis, Pagetic disease, fracture, heterotropic ossification, osteolysis, etc., since the compound can be selectively incorporated into the bone system and can be rapidly excreted into urine. In case of applying a radiolabeled compound of the present invention for bone scintigraphy to find the diseased position of bone tumor, the compound is administered intravenously to mammals including human being, then the distribution of radioactivity in the whole body are determined by use of an instrument (e.g. gamma ray camera) commonly known in the diagnostic field.

A compound of the present invention can be applied for the purposes of therapy for bone pain palliation, chronic rheumatic arthritis and inflammatory osteonosis such as low back pain and the like, and also applied as carcinostatic agents for preventing bone metastasis of tumors and the like. Additionally, a radiolabeled bisphosphonic acid derivative of the present invention can be used for diagnostic purposes of evaluating pharmacological effects such as selection of drugs and judgement of effects of drugs, etc.

As to the administration forms of drugs, bisphosphonic acid derivative of the present invention is provided as in the form of an aqueous solution or lyophilized preparation thereof, and can be provided as a kit form for labeling the compound with a radioactive nuclide by supplying the aqueous solution or lyophilized preparation comprising reducing agents, stabilizing agents and the like. The kit form for labeling the compound with a radioactive nuclide comprising a bisphosphonic acid derivative of the present invention is preferably supplied as in the form of a lyophilized preparation. In case of using, the lyophilized preparation is dissolved in a suitable diluent and labeled with a radioactive nuclide, then administered. The aqueous solution containing the above-mentioned bisphosphonic acid derivative can be administered after formulating by conventional methods used in pharamceutical practice or by labeling with a radioactive transition metal in the presence of a non-metallic reducing agent according to the present invention.

In case of radiohalogenation of the above-mentioned bisphosphonic acid derivative, a precursor which is previously substituted with a halogen or a metalloalkyl group can be used. As to the halogen, fluorine, bromine, iodine, etc. can be used, and as to the metalloalkyl group, trialkyl tin and the like represented by the formula $Sn(R_3)$ can be exemplified, and as to the alkyl group, such as methyl group, ethyl group, propyl group, butyl group can be used. Preferably, trimethyl tin or tributyl tin may be used.

In conducting the radiohalogenation using the precursor being previously substitued a bisphosphonic acid derivative with a halogen or metalloalkyl group, the kit preparation for radiolabeling as in the form of lyophilized or solution comprising the above-mentioned precursor can be used. The radiohalogenation of the precursor may be conducted by methods known in the art, such as substitution reaction or exchange reaction. Conventionally used additives such as oxidizing agents, stabilizing agents, buffering agents, vehicles, etc. may be added to the above-mentioned kit preparation for radiolabeling. For example, if necessary, chroramine T, hydrogen peroxide and the like can be added as the oxidizing agents in conducting the labeling reaction. This labeling reaction may be conducted by a known method, and temperature, concentration, pH and other conditions are not specifically restricted.

In conducting labeling with a radioactive transition metal, reducing agents to be used for chemical reduction of peracid such as pertechnetate (Tc-99m) and the like, generally metals such as tin, zinc, iron, etc. or metal compounds such as chromium chloride, chromium acetate, etc. or combinations of tin chloride, tin fluoride, etc. with organic acid or inorganic acid may be used. Further, it is not limited to metal compounds, thus, non-metallic reducing agents, such as sodium diphenylphosphinobenzene-3-sulfonate, formamidinesulfonic acid or glucoheptanoic acid and the like can be used. Dithionic acid, sodium hydrogensulfite can also be used. Additionally, by use of a compound, for example, organic acids such as gluconic acid, ascorbic acid, citric acid or the like, carbohydrate such as mannose, which forms relatively unstable complex, a compound of the present invention can be labeled with radioactive transition metal through ligand exchange reaction. In this case, the reaction conditions such as temperature, concentration, pH and others are not specifically restricted, and the reaction can be conducted at an ambient temperature or under heating, and the reducing agent may be used suitably depend on the reaction conditions.

Further, a pharmaceutical preparation of the present invention may comprise physiologically acceptable buffering agents (e.g., physiological saline, a pH controlling agents, such as acetic acid, phosphoric acid, carbonic acid, tris(hydroxymethyl)aminomethane, and the like) and other physiologically acceptable additives (e.g., stabilizing agents such as ascorbic acid, paraben, dissolving agents, vehicles such as D-mannitol and the like).

A compound of the present invention can be used similarly to conventional diganostic agents or therapeutic agents, for example, a liquid preparation is administered by injection to mammals including human-being. Administrative dosage of the compound is substantially similar to that of conventional diagnostic or therapeutic agents, the diagnostic agent is administered in a range of about 3 to 25 MBq/kg, preferably 6 to 12 MBq/kg, and the therapeutic agent is administered depending on kind of radioactive nuclide. The administrative dosage may be adjusted suitably depending on kind of the compounds, kind of the radioactive nuclides, age of the patient, body wight of the paitent, symptoms, method of administration, combined use with other drugs, and other factors.

EXAMPLES

The present invention will be explained in detail by illustrating with the following Examples, but the invention will not limited within these Examples. Further, analysis of the compounds were conducted by methods widely known in the art.

In the Examples, NMR spectra were obtained on JEOL GSX270 (manufactured by JEOL LTD.).

Abbreviations used in the Examples are as follows.

| | |
|---|---|
| WSC | 1-ethyl-3-(3-diethylaminopropyl)carbodiimide hydrochloride |
| WSCD | 1-ethyl-3-(3-diethylaminopropyl)carbodiimide |
| TMSI | triinethylsilyl iodide |
| TMSBr | trimethylsilyl bromide |
| Boc- | t-butoxycarbonyl |
| Fmoc- | 9-fluorenylmethoxycarbonyl |
| Bzl | benzyl |
| Bz | benzoyl |
| DBU | 1,8-diazabicyclo[5.4.0]-7-undecene |
| DTPA | diethylenetriamine pentaacetic acid |
| BMS | succinimidyl-S-benzoylmercaptoacetic acid |
| HOBt | 1-hydroxytriazol |
| $Et_3N$ | triethylamine |
| $^iPr_2NEt$ | diisopropylethylamine |
| DMF | N,N'-dimethylformamide |
| TFA | trifluoroacetic acid |
| PTLC | preparative thin-layer chromatography |
| HPLC | high performance liquid chromatography |
| THF | tetrahydrofuran |
| AcOEt | ethyl acetate |
| Peptides | indicated with three letters |

Example 1

Synthesis of N-(3,3-diphosphonopropionyl)glycine and Labeling thereof (1) Synthesis Scheme of synthesis is shown as follows.

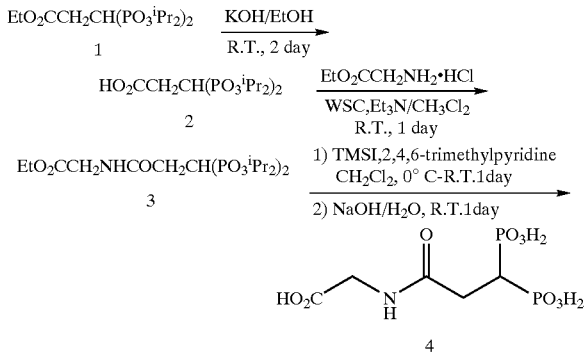

Potassium hydroxide (1.47 mmol, 0.097 g) was added to ethanol solution of compound 1 (0.98 mmol, 0.425 g) obtained by a known method, e.g., method of O. T. Quimby (O. T. Quimby, et al., Organometal. Chem., 1968, 13, 199), and the reaction mixture was stirred at room temperature for 1 day. Next, ethanol was distilled away, the residue was dissolved by adding 20 mL of saturated aqueous NaCl solution, the resulting solution was washed twice with 20 mL of ethyl acetate, then acidified with saturated aqueous $KHSO_4$ solution, and extracted three times with 40 mL of ethyl acetate, then dried over $Na_2SO_4$. The resulting extract was filtered, and concentrated to give compound 2 (70% yield). Physicochemical properties are shown below.

$^1$H-NMR (270 MHz, $CDCl_3$, δ): 1.36 (m, 24H), 2.76–3.02 (m, 3H), 4.77 (m, 4H).

$^{13}$C-NMR (67.5 MHz, $CDCl_3$): 23.8, 24.0, 24.1 (t, $J_{CP}$=6 Hz), 30.8 (t, $J_{CP}$=4 Hz), 34.2 (t, $J_{CP}$=137 Hz), 71.8, 72.0, 72.1 (t, $J_{CP}$=4 Hz), 172.5 (t, $J_{CP}$=8l Hz).

Methylene chloride solution (2 mL) of the obtained compound 2 (0.69 mmol, 0.278 g) was cooled to 0° C., then glycine ethyl ester hydrochloride (0.94 mmol, 0.132 g), $Et_3N$ (0.89 mmol, 0.115 mL) and WSC (0.76 mmol, 0.146 g) were added thereto, the resulting reaction mixture was allowed to react at 0° C. for two hours and further at room temperature for 16 hours. Methylene chloride was distilled away, the residue was dissolved in 20 mL of ethyl acetate, and the solution was washed successively with 10 mL each of saturated aqueous $KHSO_4$ solution, saturated aqueous NaCl solution, saturated aqueous $NaHCO_3$ solution, saturated aqueous NaCl solution, and dried over $Na_2SO_4$. The resulting extract was filtered and concentrated to give compound 3 (0.292 g, 0.61 mmol)(88% yield).

$^1$H-NMR (270 MHz, $CDCl_3$, δ): 1.26–1.36 (m, 27H), 2.74 (td, 2H, J=6 Hz, $J_{HP}$=17 Hz), 2.99 (tt, 1H, J=6 Hz, $J_{HP}$=24 Hz), 4.77 (m, 4H), 4.20 (BR t, 1H).

$^{13}$C-NMR (67.5 MHz, $CDCl_3$): 14.1, 23.8, 23.9, 24.1, 24.2 (t, $J_{CP}$=6 Hz), 32.4 (t, $J_{CP}$=4Hz), 35.1 (t, $J_{CP}$=137 Hz), 41.7, 61.5, 71.3, 71.4, 71.6, 71.7 (t), 168.8, 170.2.

The obtained compound 3 (0.21 mmol, 0.100 g) was put into a round bottom flask of 50 ml together with a stirring bar, the air in the flask was displaced with argon gas, and dissolved in 10 ml of anhydrous methylene chloride, then 2,4,6-trimethylpyridine (0.42 mmol, 0.051 g) was added followed by TMSI (1.05 mmol, 0.210 g) at 0° C., stirred for 1 hour, then allowed to react at room temperature for 20 hours. 20 mL of water was added to the reaction mixture, and stirred at room temperature for 24 hours. The water layer was washed in 5 times with 30 mL each of methylene chloride, then sodium hydroxide (1.58 mmol, 0.097 g) was added and allowed to react for 24 hours. The resulting reaction mixture was acidified by passing through a cation exchange resin and concentrated to give N-(3,3-diphosphonopropionyl)glycine (0.17 mmol, 0.05 g) (81% yield).

$^1$H-NMR (270 MHz, $D_2O$, TSP): 2.76–2.97 (m, 3H, P—CHCH$_2$), 3.89 (s, 2H, HO$_2$C—CH$_2$—N).

$^{13}$C-NMR (67.5 MHz, $D_2O$, TSP): 38.2 (t, $J_{CP}$=122 Hz, P—C—P), 34.4 (t, $J_{CP}$=4Hz, P—C—C), 179.3 (t, $J_{CP}$=8 Hz, NHCO), 176.6 (S, —COOH).

(2) Labeling with 99m-Technetium

A kit was prepared by adding L-ascorbic acid (1.51 μmol) and stannic chloride (II) (0.18 μmol) to N-(3,3-diphosphonopropionyl)glycine (0.34 μmol). $^{99m}TcO_4^-$ solution was added to the kit, and allowed to stand at room temperature, then heated at 80° C. for 30 minutes, a labeled product having radiochemical purity over 99% was obtained.

Example 2

Synthesis of 2-(2-iodobenzamide)-1,1-diphosphonomethane and Labeling thereof (1) Synthesis Synthesis scheme is shown as follows.

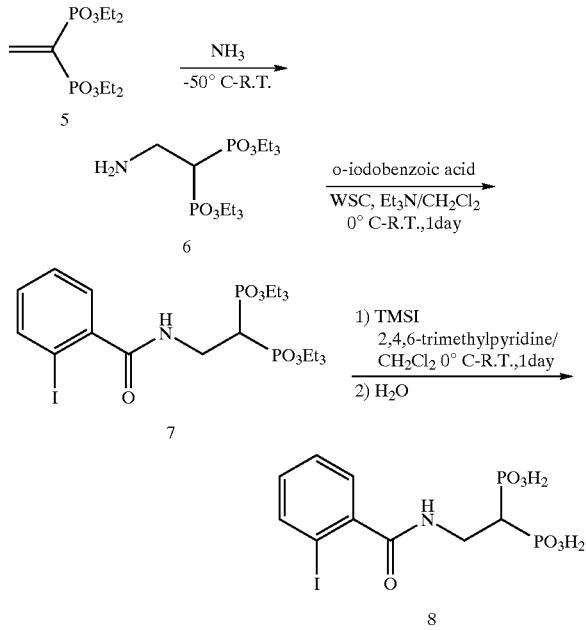

Compound 5 (3.15 mmol, 0.95 g) obtained by known method, e.g., method of Degenhardt, et al. (Degenhardt, C. R., et al.: J. Org. Chem., 1986, 51, 3488) was put into a three-necked flask, the flask was cooled to −50° C. and a liquid ammonia was charged therein, then reaction was conducted for 5 hours. The reaction mixture was slowly brought to room temperature overnight, and simultaneously the excess of ammonia was evaporated. A crude product obtained was dissolved in chloroform and the resultant solution was washed with water, and dried over $Na_2SO_4$ and concentrated to provide compound 6. A solution compound 6 (3.15 mmol, 1.00 g) in dichloromethane was placed in a round-bottomed flask of 100 mL, and added o-iodobenzoic acid (2.3 mmol, 0.570 g), then was cooled to 0° C. and, then Et$_3$N (2.99 mmol, 0.303 g) and WSC (2.53 mmol, 0.485 g) were added. The resulting solution was allowed to react at 0° C. for 2 hours and at room temperature overnight. The reaction mixture was washed successively with saturated aqueous KHSO$_4$ solution, saturated aqueous NaCl solution, saturated aqueous NaHCO$_3$ solution, saturated aqueous NaCl solution and dried over Na$_2$SO$_4$ and concentrated. The crude product obtained was purified on reversed phase column chromatography to isolate compound 7 (34% Yield).

$^1$H-NMR (270 MHz, CDCl$_3$, δ): 1.33–1.40 (m, 12H), 2.74 (tt, 1H, J=6 Hz, J$_{HP}$=23 Hz), 3.91–4.13 (m, 2H), 4.16–4.30 (m, 8H), 7.06–7.31 (m, 2H), 7.34–7.39 (m, 1H), 7.47 (dd, 1H, J=2 Hz, J=8 Hz), 7.86 (d, 1H, J=8 Hz), $^{13}$C-NMR (67.5 MHz, CDCl$_3$): 16.3, 16.4, 36.0 (t, J$_{CP}$=4 Hz), 37.0 (t, J$_{CP}$=131 Hz), 62.9, 63.0, 63.1, 63.2, 92.5, 128.0, 128.1, 131.1, 139.9, 141.4, 168.8

Next, the obtained compound 7 (0.128 mmol, 0.070 g) was put together with a stirring bar in a round-bottomed flask of 50 ml, and the air in the flask was displaced with argon gas, then 10 mL of anhydrous methylene chloride and 2,4,6-trimethylpyridine (0.768 mmol, 0.093 g, 0.101 mL) were added and stirred and cooled (0° C.), then TMSBr (0.640 mmol, 0.128 g, 0.091 mL) was added thereto and the reaction mixture was allowed to stand overnight. The reaction mixture was once concentrated, and added 10 mL of water, then stirred at room temperature for 2–3 hours, and the aqueous layer was washed with methylene chloride. Then, the solution was made basic with sodium hydroxide, again washed with methylene chloride, then acidified by passing through cation exchange resin and concentrated to obtain then 2-(2-iodobenzamido)-1,1-diphosphonomethane (0.023 mmol, 0.010 g) (18% yield).

$^1$H-NMR (270 MHz, D$_2$O, TSP): 2.78 (tt, 1H, J=7 Hz, J$_{HP}$=22 Hz, P—CH—P), 3.91 (dt, 2H, J=7 Hz, J$_{HP}$=15 Hz, —N—CH$_2$), 7.19–7.25 (m, 1H, aryl), 7.42–7.52 (m, 2H, aryl), 7.95 (d, 1H, J=8 Hz, aryl).

$^{13}$C-NMR (67.5 MHz, D$_2$O, TSP): 39.7, 41.1 (t, J$_{CP}$=125 Hz, P—C—P), 94.6, 130.8, 131.4, 134.6, 142.6, 143.6, 175.3

(2) Labeling with 123-Iodine

To 2-(2-iodobenzamido)-1,1-diphosphonomethane was added H$^{123}$I and heated at 160° C. for 40 minutes, then labeled product having radiochemical purity over 99% was obtained.

Example 3

Synthesis of 2-iodo-4-(4,4-diphosphono-propionamido)hippuric acid and Labeling thereof (1) Synthesis Synthesis scheme is shown as follows.

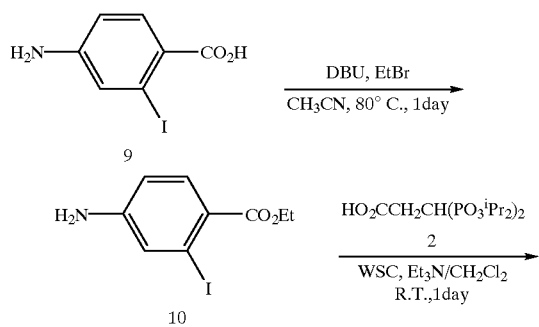

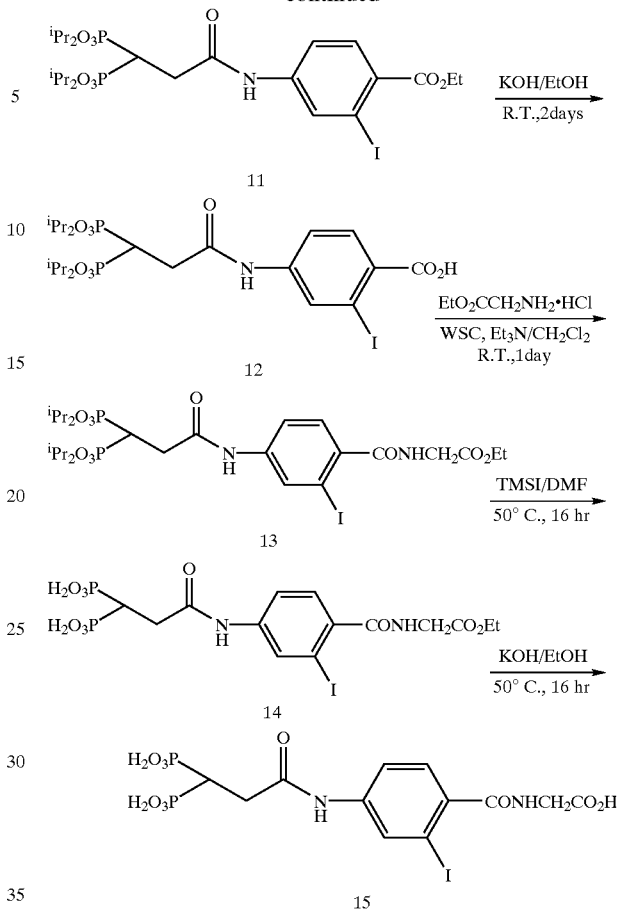

Compound 9 (0.8 mmol, 0.2 g) obtained by a known method, e.g., the method of Protiva (Protiva, Jiri et al., Collect. Czech. Chem. Commun., 1989, 54(4), 1012) was put together with a stirring bar in a round-bottomed flask of 10 mL, and was dissolved in 7 mL of anhydrous acetonitrile, then DBU (0.8 mmol, 0.12 g) and ethyl bromide (0.14 mL) were added. The reaction mixture was heated at 80° C. for 1.5 hours, and diluted with ether, then the resulting solution mixture was washed successively with water, 1N hydrochloric acid, and saturated aqueous NaHCO$_3$ solution, then dried and concentrated. The crude product was purified on a silica gel column chromatography to provide 0.17 g (0.58 mmol) of compound 10 (73% yield).

$^1$H-NMR (270 MHz, CDCl$_3$, δ): 1.38 (t, 3H, J=7 Hz), 4.05 (s, 1H), 4.33 (q, 2H, J=7 Hz), 6.62 (dd, 1H, J=3 Hz, 9 Hz), 7.30 (d, 1H, J=2 Hz), 7.77 (d, 1H, J=9 Hz).

$^{13}$C-NMR (67.5 MHz, CDCl$_3$): 14.3, 60.9, 96.4, 113.4, 122.6, 126.9, 132.9, 150.2, 165.6.

Next, compound 10 (1.4 mmol, 0.4 g) was put together with a stirring bar in a round-bottomed flask of 50 mL, and was dissolved in 20 mL of methylene chloride, then compound 2 (1.65 mmol, 0.67 g) was added. The reaction mixture was cooled at 0° C., Et$_3$N (2.16 mmol, 0.22 g) and WSC (1.82 mmol, 0.348 g) were added, then allowed to react at 0° C. to room temperature for 1 day. Next, the resulting reaction mixture was diluted to 50 mL, washed repeatedly twice with successively aqueous KHSO$_4$ solution, saturated aqueous NaCl solution, saturated aqueous NaHCO$_3$ solution in this order, then dried over Na$_2$SO$_4$ and filtered and concentrated to provide 0.65 g of crude product. Column chromatography was performed on silica gel to provide 0.363 g (0.54 mol) (38% yield) of compound 11.

$^1$H-NMR (270 MHz, CDCl$_3$, δ): 1.29–1.43 (m, 28H), 2.97 (dt, 2H, J=6 Hz, J$_{PH}$=17 Hz), 3.25 (tt, 1H, J=5 Hz, J$_{PH}$=24 Hz), 4.37 (q, 2H, J=7 Hz), 4.67–4.93 (m, 4H), 7.77 (d, 1H, J=9 Hz), 7.92 (dd, 1H, J=2 Hz, 9 Hz), 8.19 (d, 1H, J=2 Hz), 10.2 (S, 1H).

$^{13}$C-NMR (67.5 MHz, CDCl$_3$): 14.2, 23.7–24.4 (m), 32.9, 32.9 (t, J$_{PC}$=137 Hz), 61.3, 71.3–72.5 (m), 94.5, 118.2, 128.5, 131.2, 131.7, 142.7, 165.8, 168.6 (t, J$_{PC}$=8 Hz).

Compound 11 (2.0 mmol, 1.38 g) was put together with a stirring bar in a round-bottomed flask of 100 mL, and dissolved in 30 mL of ethanol, then potassium hydroxide (20 mmol, 1.32 g) was added, and reaction was conducted at room temperature for 2 days. The resulting reaction mixture was concentrated and acidified with aqueous KHSO$_4$ solution, then extracted with chloroform. The chloroform layer was dried over Na$_2$SO$_4$, then filtered and concentrated to provide a crude product of compound 12 (1.7 mmol, 1.1 g) (85% yield).

$^1$H-NMR (270 MHz, CDCl$_3$, δ): 1.28–1.42 (m, 29H), 2.95–3.28 (m, 3H), 4.70–4.92 (m, 4H), 7.90 (d, 1H, J=9 Hz), 8.09 (d, 1H, J=9 Hz), 8.23 (s, 1H), 9.61 (s, 1H).

$^{13}$C-NMR (67.5 MHz, CDCl$_3$): 23.7–24.3 (m), 33.3, 34.7 (t, J$_{PC}$=138 Hz), 71.8–72.8 (m), 95.7, 118.3, 128.0, 131.4, 132.6, 142.5, 168.1, 169.2 (t, J$_{PC}$=8 Hz).

The obtained compound 12 (1.7 mmol, 1.1 g) was put together with 40 mL of chloroform and glycine ethyl ester hydrochloride (2.5 mmol, 0.352 g) into a round-bottomed flask of 100 mL, and cooled to 0° C., then WSC (5 mmol, 0.959 g) and Et$_3$N (6 mmol, 0.61 g) were added thereto, the reaction mixture was stirred overnight at 0° C. to room temperature. The resulting reaction mixture was washed successively with saturated aqueous KHSO$_4$ solution, saturated aqueous NaCl solution, saturated aqueous NaHCO$_3$ solution, saturated aqueous NaCl solution, then dried over Na$_2$SO$_4$ and concentrated to provide 1.2 g of a crude product. Column chromatography was performed on silica gel to give compound 13 (0.78 mmol, 0.57 g) (46% yield).

$^1$H-NMR (270 MHz, CDCl$_3$, δ): 1.28–1.47 (m, 30H), 2.92 (dt, 2H, J=6 Hz, J$_{PH}$=17 Hz), 3.40 (tt, 1H, J=5.9, J$_{PH}$=24 Hz), 4.16–4.28 (m, 4H), 4.70–4.88 (m, 4H), 7.02 (t, 1H, J=5 Hz), 7.16 (dd, 1H, J=1 Hz, 9 Hz), 7.79–7.82 (m, 2H), 10.2 (s, 1H).

$^{13}$C-NMR (67.5 MHz, CDCl$_3$): 14.1, 23.9–24.2 (m), 32.7 (t, J$_{PC}$=137 Hz), 41.7, 61.4, 71.2–72.2 (m), 92.1, 118.3, 128.3, 129.8, 134.9, 141.3, 168.6 (t, J$_{PC}$=8 Hz), 169.4, 169.7.

Compound 13 (1.34×10$^{-4}$ mol, 0.098 g) was put together with a stirring bar in a round-bottomed flask of 10 mL, and dissolved in 2 mL of DMF, the air in the flask was displaced with argon gas. 2,4,6-Trimethylpyridine (1.2 mmol, 0.15 g) and TMSI (1.2 mmol, 0.24 g) were added thereto, and the reaction was conducted at 50° C. for 16 hours. 1 mL of water was added to the reaction mixture, and the resulting mixture was stirred at room temperature for 1 hour. The aqueous layer was washed three times with methylene chloride, then the washed aqueous layer was made basic with 1N sodium hydroxide. Further, the aqueous layer was washed with methylene chloride, acidified by passing through a cation exchange resin, then concentrated, 2-iodo-4-(4,4-diphosphonopropionamido)hippuric acid (8.2×10$^{-5}$ mol, 0.044 g) (yield: 61%) was obtained.

$^1$H-NMR (270 MHz, D$_2$O, TSP): 2.38–3.14 (m, 3H), 4.18 (s, 2H), 7.41 (d, 1H, J=8 Hz), 7.53 (dd, 1H, J=2 Hz, 8 Hz), 8.04 (d, 1H, J=2 Hz).

$^3$C-NMR (67.5 MHz, D$_2$O, TSP): 35.4, 37.0 (t. J$_{PC}$=129 Hz), 44.4, 94.6, 123.3, 131.5, 134.6, 139.1, 142.5, 174.2 (t, J$_{PC}$=8 Hz), 175.3, 175.7

(2) Labeling with 123-Iodine

Similar to Example 2, labeling of 2-iodo-4-(4,4-diphosphonopropionamido)hippuric acid with 123-iodine was conducted, a labeled product having radiochemical purity over 99% was obtained.

Example 4

Synthesis of 3,6-bis(carboxymethyl)-9-(((2,2-diphosphonoethyl)carbamoyl)methyl)-3,6,9-triazaundecanedicarboxylic acid and Labeling thereof (1) Synthesis Synthetic scheme is shown as follows.

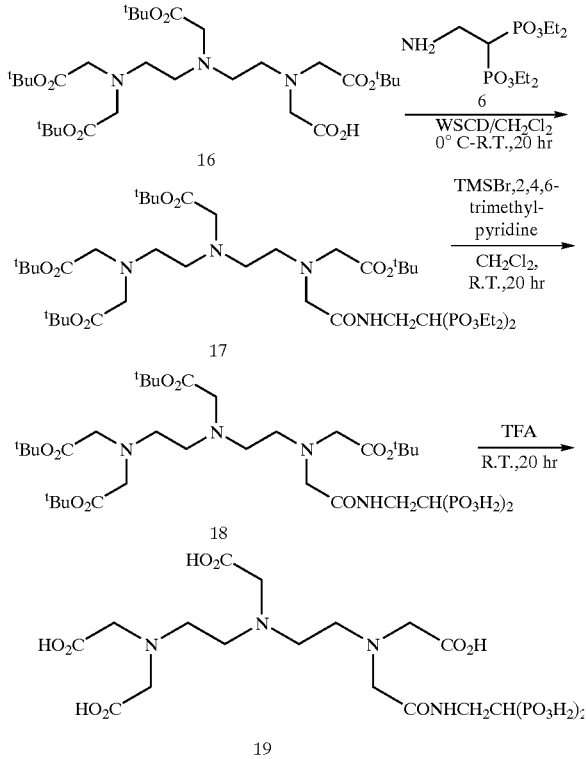

Mono-t-butyl 3,6,9-tris((t-butoxycarbonyl)-methyl)-3,6,9-triazaundecanedicarboxylate (compound 16) was obtained by a known method, e.g., the method of Arano (Y. Arano et al., J. Med. Chem., 39, (18), 3451–3460, (1996)). The compound 16 (923 mg, 1.5 mmol) and compound 6 (645 mg, 2.0 mmol) were dissolved in 10 mL of methylene chloride, under an ice-cooling condition, WSCD (380 mg, 2.0 mmol) was added thereto. The reaction mixture was stirred for 20 hours, then 100 mL of chloroform was added, and washed with 20 mL of water, the solvent of the organic layer was evaporated under reduced pressure. The residue thus obtained was purified on a silica gel column chromatography (Silica gel 60, 30 g, eluted with CHCl$_3$/EtOH= 100/3) to provide compound 17 (288 mg, 0.31 mmol, 21% yield) as yellow oil.

$^1$H-NMR (270 MHz, CDCl$_3$, δ): 1.35 (12H, t, J=7 Hz, —CH$_3$), 1.45 (36H, s, —$^t$Bu×4), 2.77 (9H, m, —CH— and —NCH$_2$CH$_2$N—×2), 3.30 (2H, s, —NCH$_2$CO—), 3.31 (2H, s, —NCH$_2$CO—), 3.34 (2H, s, —NCH$_2$CO—), 3.36 (2H, s, —NCH$_2$CO—), 3.43 (2H, s, —NCH$_2$CO—), 3.78 (2H, m, —NHCH$_2$—), 4.20 (8H, m, —POCH$_2$—×4), 8.1 (1H, BR s, —NH—).

Next, compound 17 was dissolved in methylene chloride, under an atmosphere of argon gas, 2,4,6-trimethylpyridine and TMSBr were added thereto, reaction was conducted at room temperature for 20 hours. After removal of the solvent by distillation, water was added and neutralized with 1N NaOH, then washed with mehylene chloride. The aqueous layer was subjected to desalting, and the solvent was distilled away to give compound 18.

Compound 18 (386 mg) was dissolved in 3.0 mL of TFA. The solution was stirred at room temperature for 2.5 hours, then the solvent was distilled away, the residue thus obtained was subjected to crystallization with water-methanol, then 3,6-bis(carboxymethyl)-9-(((2,2-diphosphonoethyl) carbamoyl)methyl)-3,6,9-triazaundecanedicarboxylic acid (compound 19) (56 mg) was obtained as pale yellow crystals.

$^1$H-NMR (270 MHz, D$_2$O, TSP): 2.50 (1H, m, —CH—), 3.26 (4H, d, J=6 Hz, —NCH$_2$—×2), 3.44 (2H, t, J=6 Hz, —NCH$_2$—), 3.52 (2H, t, J=6 Hz, —NCH$_2$—), 3.72 (2H, s, —NCH$_2$CO—), 3.77 (2H, m, —NHCH$_2$—), 3.92 (2H, s, —NH$_2$CO—), 4.01 (6H, s, —NCH$_2$CO—×3).

(2) Labeling with 111-Indium

A kit-type product was prepared by dissolving compound 19 (0.87 mg, 1.5 μmol) in 1.5 ml of 0.2M acetic acid buffer solution (pH 5.6) per one vial. $^{111}$InCl$_3$ was added to the vial and heated, then a labeled product was obtained.

(3) Labeling with 99m-Technetium by Using Stannous Chloride

A kit-type product containing compound 19 (0.87 mg, 1.5 μmol), L-ascorbic acid (0.176 mg, 0.1 μmol) and anhydrous stannous chloride (0.022 mg, 0.12 μmol) in 0.25 mL of aqueous solution per one vial, having pH 5 was prepared. To the vial, $^{99m}$TcO$_4^-$ was added and heated to obtain a labeled product.

(4) Labeling with 99m-Technetium by Using Sodium diphenylphosphinobenzene-3-sulfonate A kit-type product containing compound 19 (1.5 μmol) and sodium diphenylphosphinobenzene-3-sulfonate (1.17 μmol) in 1.65 mL of total volume of aqueous solution per one vial, having pH 4 was prepared. To the vial, $^{99m}$TcO$_4^-$ was added and heated in a boiling water bath for 30 minutes, then shaked at room temperature, a labeled product was obtained. As the result of TLC analysis, the labeling rate was over 95%.

Example 5

Synthesis of 3,9-bis(carboxymethyl)-6-(((2,2-diphosphonoethyl)carbamoyl)methyl)-3,6,9-triazaundecanedicarboxylic acid (Compound 23)

Synthesis scheme is shown as follows.

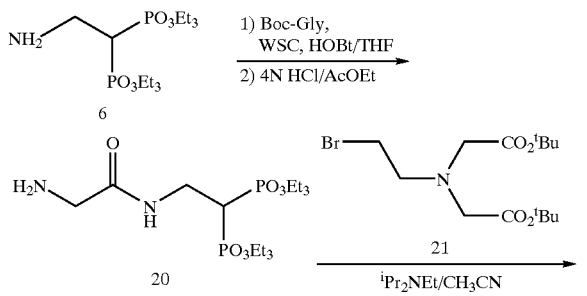

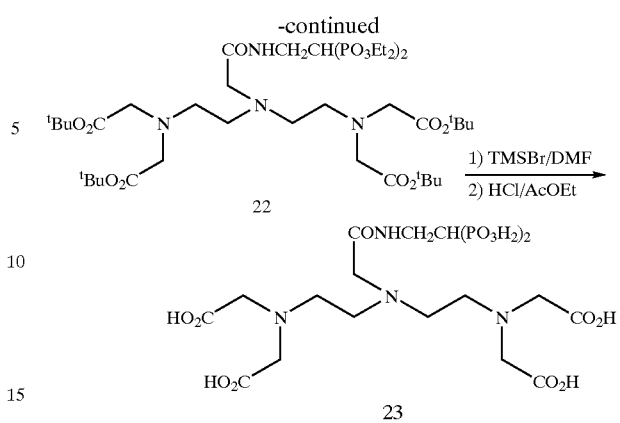

In advance, compound 21 was synthesized as follows. Sodium carbonate was added to 2-bromoethylamine ammonium bromide, the mixture was suspended in acetonitrile and stirred. t-Butyl bromoacetate was added thereto and reaction was conducted. The solvent was distilled away from the reaction mixture and the residue was extracted, the organic layer was dried and subjected to a silica gel column chromatography to give compound 21 in 40% yield.

$^1$H-NMR (270 MHz, CDCl$_3$, δ): 1.46 (18H, s, –$^t$Bu), 3.13 (2H, t, J=7 Hz, —CH$_2$CH$_2$N—), 3.44 (2H,t, J=7 Hz, —BrCH$_2$—), 3.48 (4H, s, —NCH$_2$CO—).

$^3$C-NMR (67.5 MHz, CDCl$_3$): 28.1, 30.2, 56.5, 56.6, 81.3, 170.5.

Each one equivalent of compound 6 and Boc-glycine was dissolved in THF, then 1.1 equivalent of HOBt was added thereto. Under an ice-cooled stirring, 1.2 equivalent of WSC was added, the reaction was conducted overnight. The reaction mixture was worked up to give Boc-protected product of compound 20 in 36% yield. Next, the Boc-group was deprotected by adding 4N HCl/AcOEt to provide compound 20 quantitatively. Then the previously synthesized compound 21 was added in amount of 2.4 equivalents to compound 20, reaction was conducted by adding $^i$Pr$_2$NEt in acetonitrile solvent. The reaction mixture was worked up to give compound 22 in 16% yield. Compound 22 was dissolved in DMF, deesterification of the phosphoric acid was conducted by adding TMSBr. The reaction mixture was worked up, then deesterification of the carboxylic acid was conducted by adding 4N HCl/AcOEt. The resulting reaction mixture was purified to give 3,9-bis(carboxymethyl)-6-(((2,2-diphosphonoethyl)carbamoyl)methyl)-3,6,9-triazaundecanecarboxylic acid (compound 23) in 6% yield.

Example 6

Synthesis of N-mercaptoacetyl-[2-[4-(4,4-diphosphonopropionamido)butyl]glycyl]glycylglycine (Compound 27) and Labeling thereof (1) Synthesis Synthesis scheme is shown as follows.

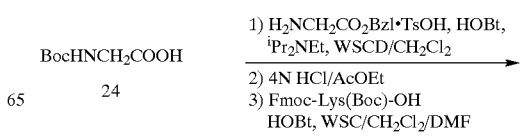

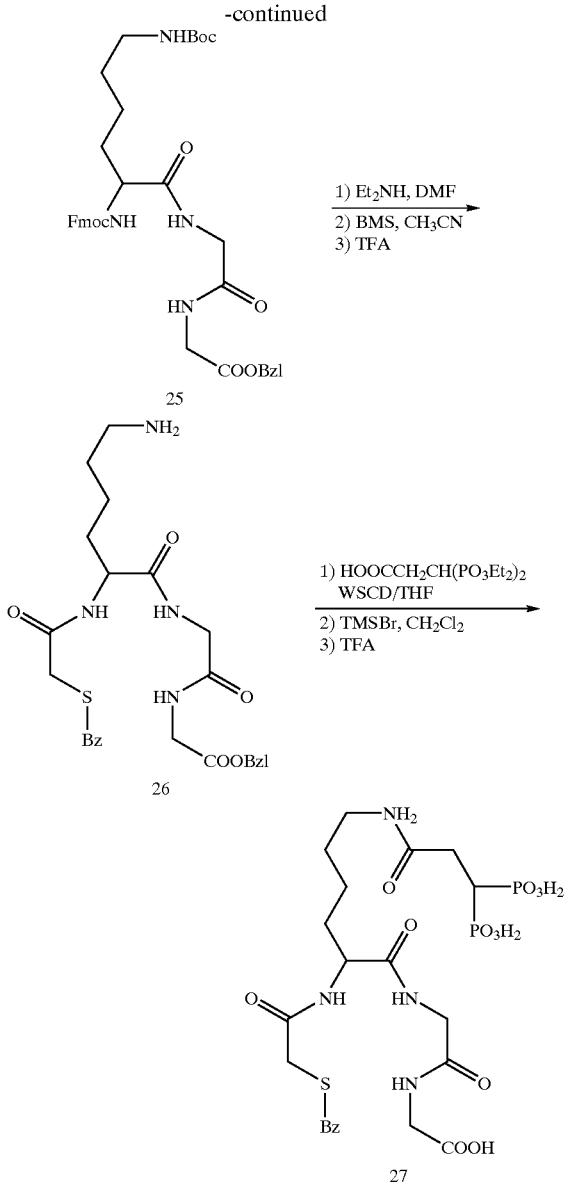

solved in 36 mL of acetone. Under cooling in an ice-bath, WSC (5.76 g, 30.0 mmol) was added and dissolved by adding 40 mL of methylene chloride. Two hours later, the reaction mixture was allowed to stand at room temperature over night. The solvent was distilled away, the residue was purified on a silica gel column chromatography (eluted with chloroform) to give BMS (7.72 g, 26.3 mmol, 88% yield) as white crystals.

Boc-glycine (5.28 g, 30.1 mmol), HOBt (4.07 g, 30.1 mmol) and glycinebenzyl ester p-toluenesulfonate (10.02 g, 29.7 mmol) were dissolved in methylene chloride, then $^i$Pr$_2$NEt (3.89 g, 30.1 mmol) was added thereto. Under stirring in an ice-bath, WSCD (5.60 g, 36.1 mmol) was added dropwise. Reaction was conducted for 20 hours and the solvent was distilled away, the resulting residue was dissolved in 200 mL of AcOEt, and washed successively with 100 mL each of 5% aqueous citric acid, water, 5% aqueous NaHCO$_3$ solution and water in this order. The organic layer was dried over Na$_2$SO$_4$, the solvent was evaporated to give Boc-glycylglycylbenzyl ester in 78% yield. Subsequently, Boc-group was deprotected by adding 4N HCl/AcOEt, then glycylglycylbenzyl ester was obtained quantitatively.

Next, the glycylglycylbenzyl ester (2.64 g, 10.2 mmol) obtained in the previous step, Fmoc-lysine(Boc) (4.74 g, 10.1 mmol) and HOBt (1.38 g, 10.2 mmol) were suspended in 100 mL of methylene chloride and 5 mL of DMF. Under cooling in an ice-bath, WSCD (1.88 g, 12.1 mmol) was added dropwise, and washed with 4 mL of methylene chloride. 18 Hours later, the solvent was distilled away, the residue was dissolved in ethyl acetate, and washed successively with 10% aqueous citric acid, water, 5% aqueous NaHCO$_3$ solution and water. The organic layer was dried over Na$_2$SO$_4$, and the solvent was evaporated. The residue (15 g) was purified on a silica gel column chromatography (250 g, CHCl$_3$/MeOH=100/3) to give compound 25 (6.67 g, 9.98 mmol, 98% yield) as white crystals.

Thus obtained compound 25 (3.36 g, 4.93 mmol) was dissolved in 50 mL of DMF, and added 5 mL of diethylamine at room temperature. 2 Hours after, the solvent was evaporated, the residue was purified on PTLC (CHCl$_3$/MeOH=10/1) to give pale yellow crystals (2.12 g, 4.71 mmol, 95% yield). The pale yellow crystals (878.7 mg, 1.95 mmol) was dissolved in 30 mL of acetonitrile, then previously synthesized BMS (648.3 mg, 2.2 mmol) was added. After 16 hours, the solvent was evaporated, the residue was purified on PTLC (CH$_3$Cl/MeOH=10/1) to provide white crystals (1.07 g, 1.70 mmol, 87% yield). The white crystals (1.89 g, 3.00 mmol) was suspended in 25 mL of methylene chloride, under stirring at room temperature, 15 mL of TFA was added dropwise. After 10 minutes, the solvent was evaporated under reduced pressure, the residue was extracted with 25 mL of AcOEt and washed with saturated aqueous NaHCO$_3$ solution. The organic layer was dried over Na$_2$SO$_4$ and the solvent was evaporated to give compound 26 (1.32 g, 2.49 mmol, 83% yield) as white crystals.

Compound 26 and ethyl ester of compound 2 were dissolved in THF, then WSCD was added, under cooling an ice-bath, and reaction was conducted, a colorless oil (48% yield) was obtained. The product was dissolved in methylene chloride under stirring in a stream of argon gas, then TMSBr was added thereto under an ice-cooling and reaction was conducted for 2 days. After evaporating the solution, the residue was dissolved in a small amount of methanol, then diethyl ether was added so as to precipitate white crystals. Next, TFA was added to the white crystals and stirred at room temperature for 3 days to eliminate benzyl group. The In advance, succinimidyl-S-benzoylmercaptoacetic acid (BMS) was synthesized as follows. Two-layer system of toluene (75 mL) and water (75 mL) was cooled in an ice-water bath, sodium hydroxide (8.86 g, 221.5 mmol) was added thereto. Next, mercaptoacetic acid (9.22 g, 100 mmol) was added dropwise and washed with 5 mL of water. Further, benzoyl chloride (14.61 g, 100.3 mmol) was added dropwise, and washed with 5 mL of toluene. The reaction was conducted with stirring at about 5° C. for 30 minutes, then at room temperature for 3.5 hours. The reaction mixture was subjected to separation, the organic layer was extracted in 3 times with 10 mL of water, and the aqueous layers were combined together. Under stirring, 12 mL of concentrated hydrochloric acid was added dropwise to the aqueous layer to adjust pH 1–2, and the crystals formed were collected by filtration. The crystals were dried in a desiccator, then washed with hexane, and dissolved in ethyl acetate. The solvent was distilled away to give S-benzoylmercaptoacetic acid (19.19 g, 97.8 mmol, 98% yield) as colorless needle-like crystals.

Next, S-benzoylmercaptoacetic acid (5.89 g, 30.0 mmol) and N-hydroxysuccinimide (3.89 g, 33.8 mmol) were disresulting product was purified on HPLC (ODS, CH₃CN/H₂O), then Bz-product of N-mercaptoacetyl-2-[4-(4,4-diphosphonopropionamido)butyl]glycylglycylglycine was obtained.

(2) Labeling with 99m-Technetium

Physiological saline and saturated aqueous ammonia solution were added to a vial containing, 10 mmol of Bz-substituted product of N-mercaptoacetyl-2-[4-(4,4-diphosphonopropionamido)butyl]glycylglycylglycine (compound 27), then reaction for debenzoylation was conducted at room temperature. 99m-Technetium glucoheptanate, which was prepared separately, was added to the resulting vial, and the labeling reaction was conducted by heating, then a product labeled with 99m-Technetium was obtained.

Example 7

Formation of Monomolecular Complex (1) Mercaptoacetylglycylglycylglycine (MAG3) solution (1.5 μmol/0.2 mL), of which pH value was adjusted, was added to a commercially available HMDP kit (CLEARBONE KIT: manufactured by NIHON MEDI-PHYSICS CO., LTD./HMDP 1.5 μmol) in the amount of equal equivalent. Homogeneous solution was prepared by adding 0.3 mL of a physiological saline to dissolve the contents in the kit. Reaction was conducted to make the whole volume in the kit to 1.0 mL by adding 0.5 mL of $^{99m}TcO_4^-$ solution eluted from a generator. The reaction mixture was allowed to stand at room temperature for 30 minutes, and was subsequently heated in a boiling water-bath for 30 minutes. Labeling rates were determined by means of a TLC after finished each reactions. The pH of the reaction mixtures after finished the reactions were 5.6, 6.7 and 7.6, respectively. The results of experiments are shown in Table 1 as follows.

TABLE 1

| Reaction condition | Labeling rates (%) with 99m-Technetium to HMDP and MAG3 | | | | | |
|---|---|---|---|---|---|---|
| | pH 5.9 | | pH 6.7 | | pH 7.6 | |
| | HMDP | MAG3 | HMDP | MAG3 | HMDP | MAG3 |
| At room temperature (for 30 min.) | 100 | 0.0 | 44~52 | 0.0 | 26~53 | 1.1 |
| By heating (for 30 min.) | 67~100 | 16.5 | 28~37 | 27.0 | 13~37 | 33.4 |

As can be seen from the data shown in Table 1, when conducting the labeling reaction at low pH, then HMDP product being labeled with 99m-Technetium was formed advantageously in high rate, while MAG3 product being labeled with 99m-Technetium was formed in extremely low rate. On the contrary, when conducting the labeling reaction by heating, then formation of HMDP product being labeled with 99m-Technetium is inhibited, while MAG3 product being labeled with 99m-Technetium is formed in high rate. Thus, there can be proved that when conducting the reaction for labeling MAG3 derivative with technetium at high pH and by heating, then MAG3 is selectively labeled with 99m-Technetium and monomolecular complex having free type of bisphosphonic acid structure can be formed.

(2) Kit products for labeling complex were prepared by mixing equal equivalent (1.5 μmol) of each of HMDP and monosubstituted DTPA (DTPA*), wherein DTPA was bonded to phenethylamine through the amino bonding. 0.4 mL each of $^{111}$In-indium chloride was added to each one of the two kits (dissolved in 0.5 mL), and reactions were conducted, respectively by allowing to stand at room temperature for 30 minutes, or by heating (at 121° C.) in an autoclave for 20 minutes. After finished the reactions, labeling rates (%) were determined by means of TLC and electrophoresis. As the control experiments, labeling of HMDP and DTPA* with 111-Indium was carried out respectively. Test results are shown in Table 2 as follows.

TABLE 2

| | Labeling rates (%) with 111-Indium to HMDP and DTPA* | | | |
|---|---|---|---|---|
| | Mixed solution | | Control solution | |
| | By heating | Room temp. | (At room temp.) | |
| | | | HMDP | DTPA* |
| $^{111}$In-labeled HMDP | 1.8 | 1.9 | 46 | — |
| $^{111}$In-labeled DTPA | 84 | 97 | — | 98 |
| $^{111}$InCl₃ | 0.4 | 0.7 | 52 | 0.6 |
| $^{111}$In-others | 12 | 0.8 | — | 0.9 |

DTPA*: monosubstituted DTPA

As can be seen from the data shown in Table 2, DTPA was labeled advantageously with 111-Indium in comparison with HMDP. Thus, DTPA derivative was selectively labeled with 111-Indium chloride at room temperature, and the formation of monomolecular complex having free type bisphosphonic acid structure was proved.

As explained the above, by selecting suitable pH and heating conditions, and by applying the ability of forming complex with radioactive transition metal nuclide, the desired monomolecular complex, wherein free type of bisphosphonic acid structure may be kept in the bisphosphonic acid derivative, can be obtained by selectively forming the complex with metal coordinating functional group in the bisphosphonic acid derivative, provided that bisphosphonic acid group is not participate in the formation of complex with a radioactive transition metal.

Example 8

Determination of Biodistribution

SD strain rats (female, age in 8–9 weeks, n=3) were used with free access to water and food ad libitum, and anesthetized with Ravonal, (a trade name of thiopental sodium, manufactured by Tanabe Seiyaku Co., Ltd.), then the test sample solution was administered to the caudal vein. The test rats were killed by bleeding during the blood samples were taken from the abdominal aorta at each times of sampling after the administration. The organs of interest were excised. After measured the weights of these samples, the radioactivities were determined, and biodistributions were calculated. The results of determination of biodistribution relating to the labeled compounds obtained in Examples 1, 2 and 4 and the labeled compounds of methanediphosphonic acid (MDP) used as reference examples are shown in Tables 3 to 7. Determination results are indicated as %ID/g, and determination results of urine are indicated as %ID.

TABLE 3

Biodistribution of N-(3,3-diphosphonopropionyl)glycine labeled with 99m-Technetium
SD-rats (Female, age in 8 weeks) n = 3 (% ID/g)

| Organs | 15 Minutes | 120 Minutes |
| --- | --- | --- |
| Femur and Tibia | 3.014 ± 0.377 | 3.552 ± 0.327 |
| Liver | 0.159 ± 0.009 | 0.068 ± 0.003 |
| Blood | 0.599 ± 0.103 | 0.089 ± 0.037 |
| Kidney | 3.225 ± 0.543 | 0.762 ± 0.279 |
| Urine (% ID) | 29.69 ± 0.14 | 48.15 ± 1.50 |

TABLE 4

Biodistribution of 2-(2-iodobenzamido)-1,1-diphosphomethane labeled with 123-Iodine
SD-rats (Female, age in 9 weeks) n = 3 (% ID/g)

| Organs | 15 Minutes | 120 Minutes |
| --- | --- | --- |
| Femur and Tibia | 3.423 ± 0.302 | 3.714 ± 0.474 |
| Liver | 0.495 ± 0.078 | 0.380 ± 0.037 |
| Blood | 0.717 ± 0.159 | 0.042 ± 0.006 |
| Kidney | 2.751 ± 0.951 | 1.070 ± 0.539 |
| Urine (% ID) | 19.55 ± 0.72 | 41.54 ± 4.19 |

TABLE 5

Biodistribution of 3,6-bis(carboxymethyl)-9-(((2,2-diphosphonoethyl)carbamoyl)methyl)-3,6,9-triazaundecanedicarboxylic acid labeled with 111-Indium
SD-rats (Female, age in 8 weeks) n = 3 (% ID/g)

| Organs | 15 Minutes | 120 Minutes |
| --- | --- | --- |
| Femur and Tibia | 2.777 ± 0.311 | 2.739 ± 0.385 |
| Liver | 0.081 ± 0.010 | 0.081 ± 0.006 |
| Blood | 0.519 ± 0.025 | 0.238 ± 0.025 |
| Kidney | 2.413 ± 0.997 | 1.551 ± 2.157 |
| Urine (% ID) | 26.04 ± 9.29 | 40.31 ± 9.02 |

TABLE 6

Biodistribution of 3,6-bis(carboxymethyl)-9-(((2,2-diphosphonoethyl)carbamoyl)methyl)-3,6,9-triazaundecanedicarboxylic acid labeled with 99m-Technetium by using stannous chloride
SD-rats (Female, age in 8 weeks) n = 3 (% ID/g)

| Organs | 15 Minutes | 120 Minutes |
| --- | --- | --- |
| Femur and Tibia | 2.417 ± 0.495 | 3.089 ± 0.340 |
| Liver | 0.108 ± 0.046 | 0.038 ± 0.017 |
| Blood | 0.621 ± 0.239 | 0.040 ± 0.006 |
| Kidney | 3.294 ± 1.616 | 0.939 ± 0.510 |
| Urine (% ID) | 28.64 ± 5.55 | 54.91 ± 1.96 |

TABLE 7

Biodistribution of 3,6-bis(carboxymethyl)-9-(((2,2-diphosphonoethyl)carbamoyl)methyl)-3,6,9-triazaundecanedicarboxylic acid labeled with 99m-Technetium by using sodium diphenylphosphinobenzene-3-sulfonate
SD-rats (Female, age in 8 weeks) n = 3 (% ID/g)

| Organs | 15 Minutes | 120 Minutes |
| --- | --- | --- |
| Femur and Tibia | 2.643 ± 0.182 | 2.922 ± 0.187 |
| Liver | 0.187 ± 0.041 | 0.153 ± 0.057 |

TABLE 7-continued

Biodistribution of 3,6-bis(carboxymethyl)-9-(((2,2-diphosphonoethyl)carbamoyl)methyl)-3,6,9-triazaundecanedicarboxylic acid labeled with 99m-Technetium by using sodium diphenylphosphinobenzene-3-sulfonate
SD-rats (Female, age in 8 weeks) n = 3 (% ID/g)

| Organs | 15 Minutes | 120 Minutes |
| --- | --- | --- |
| Blood | 0.463 ± 0.056 | 0.086 ± 0.063 |
| Kidney | 1.519 ± 1.139 | 0.630 ± 0.307 |
| Urine (% ID) | 37.996 ± 5.927 | 54.927 ± 4.073 |

TABLE 8

Biodistribution of MDP labeled with 99m-Technetium
SD-rats (Female, age in 7 weeks) n = 3 (% ID/g)

| Organs | 15 Minutes | 120 Minutes |
| --- | --- | --- |
| Femur and Tibia | 2.881 ± 0.267 | 3.272 ± 0.29 |
| Liver | 0.104 ± 0.019 | 0.078 ± 0.008 |
| Blood | 0.423 ± 0.012 | 0.034 ± 0.004 |
| Kidney | 7.364 ± 2.289 | 0.710 ± 0.289 |
| Urine (% ID) | 23.07 ± 3.985 | 49.615 ± 0.657 |

As can be seen from the data shown in Tables 3–8, rapid urinary excretion was observed in any one of these compounds of the present invention, particularly 2-(2-iodobenzamido)-1,1-diphosphonomethane labeled with 123-Iodine, which is a monomolecular compound, was rapidly excreted into urine. Also, the blood clearance of this compound was relatively rapid. Additionally, this compound was accumulated to the bone quickly, and the accumulation level to the bone did not significantly vary from 15 minutes to 120 minutes after the administration of this compound.

In conclusion, a bisphosphonic acid derivative and product thereof labeled with a radioactive nuclide was accumulated to the bone rapidly and was also rapidly excreted into urine, thus it can be said clearly that a bisphosphonic acid derivative and a product thereof labeled with a radioactive nuclide of the present invention is useful as the active ingredient of an diagnostic and therapeutic agent for bone disease.

What is claimed is:

1. A bisphosphonic acid derivative or salt thereof represented by the following formula (1):

$$R-Y-A \qquad (1)$$

wherein A is a bisphosphonic acid or salt thereof, having a P—C—P bond; Y is a bonding portion selected from the group consisting of $-(CH_2)-$, $-[(CH_2)_m(NHCO)_r(CH_2)_n]_q-$, $-[(CH_2)_m(CONH)_r(CH_2)_n]_q-$ and $-(CH_2)_o-S-(CH_2)_p-$; k, l, m, n, o, p, q and r each represents independently an integer, and k=0 or 1, l=1 to 6, m=0 to 6, n=1 to 6, o=0 to 6, p=0 to 6, q=1 to 6, and r=1 to 6; R is a group of any one of compounds selected from the group consisting of a polyaminopolycarboxylic acid, an aliphatic carboxylic acid, a mercaptoacetylpolyamino acid and a compound represented by the following formula (2),

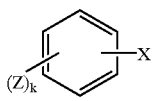
(2)

and in the formula (2), X is a halogen atom or its isotope, or an alkyl tin; Z is a group of any one of compounds selected from the group consisting of an aminocarboxylic acid, an alkylcarboxylic acid, a substituted-alkylcarboxylic acid, an alkylsulfonic acid and a substituted-alkylsulfonic acid.

2. The bisphosphonic acid derivative according to claim 1, wherein R is carboxyl group, and the compound is represented by the following formula (3):

HOOC—Y—A (3)

wherein Y and A are the same as defined in claim 1.

3. The bisphosphonic acid derivative according to claim 2, wherein the compound is represented by the following formula (4):

HOOCCH$_2$NHCOCH$_2$CH(PO$_3$H$_2$)$_2$. (4)

4. The bisphosphonic acid derivative according to claim 1, wherein the compound is represented by the following formula (5):

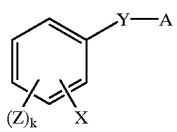
(5)

wherein A, X, Y, Z and k are the same as defined in claim 1.

5. The bisphosphonic acid derivative according to claim 4, wherein the compound is represented by the following formula (6):

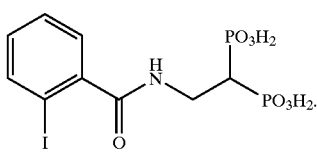
(6)

6. The bisphosphonic acid derivative according to claim 4, wherein the compound is represented by the following formula (7):

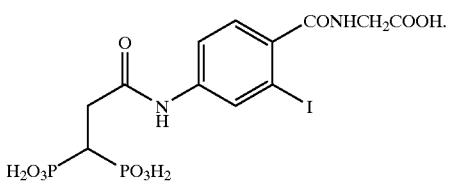
(7)

7. The bisphosphonic acid derivative according to claim 1, wherein the compound is represented by the follwing formula (8):

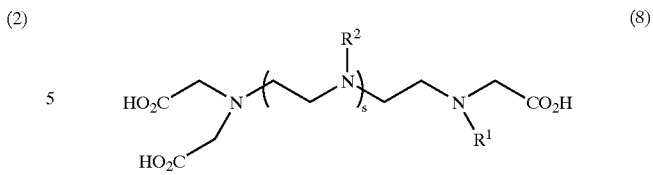
(8)

wherein Y and A are the same as defined in claim 1; $R^1$ and $R^2$ are represented by any one of Y—A or Y—COOH; when s=0, then $R^1$ is Y—A; when s=1, and $R^1$ is Y—A, then $R^2$ is Y—COOH; when $R^1$ is Y—COOH, then $R^2$ is Y—A; when s=2 to 4, and $R^1$ is Y—A, then $R^2$ is Y—COOH; and when $R^1$ is Y—COOH, then one of $R^2$ is Y—A and another one is Y—COOH.

8. The bisphosphonic acid derivative according to claim 7, wherein the compound is represented by the following formula (9):

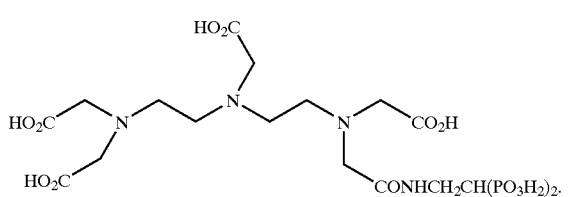
(9)

9. The bisphosphonic acid derivative according to claim 7, wherein the compound is represented by the following formula (10):

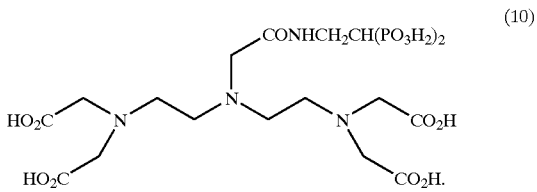
(10)

10. The bisphosphonic acid derivative according to claim 1, wherein the compound is represented by the following formula (11):

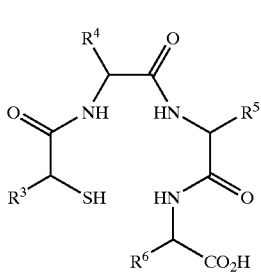
(11)

wherein $R^3$, $R^4$, $R^5$ and $R^6$ are each respectively Y—A (wherein Y and A are the same as defined in claim 1) or a hydrogen atom; when $R^3$ is Y—A, then $R^4$, $R^5$ and $R^6$ are each a hydrogen atom; when $R^4$ is Y—A, then $R^3$, $R^5$ and $R^6$ are each a hydrogen atom; when $R^5$ is Y—A, then $R^3$, $R^4$ and $R^6$ are each a hydrogen atom; and when $R^6$ is Y—A, then $R^3$, $R^4$ and $R^5$ are each a hydrogen atom.

11. The bisphosphonic acid derivative according to claim 10, wherein the compound is represented by the following formula (12):

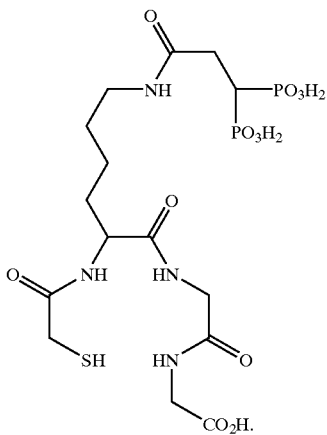

12. A bisphosphonic acid derivative labeled with a radioactive nuclide, prepared by labeling any one of bisphosphonic acid derivative according to any one of claims 1 to 11, with a radioactive nuclide.

13. The bisphosphonic acid derivative labeled with a radioactive nuclide according to claim 12, wherein R in the formula (1) of R—Y—A is a compound labeled with a radioactive halogen atom or a compound labeled with a radioactive transition metal; further, A is a free form of bisphosphonic acid or a salt thereof, which does not participate in the formation of complex with said radioactive transition metal or other metal.

14. The biophosphonic acid derivative labeled with a radioactive nuclide according to claim 12, wherein the radioactive nuclide is any one of nuclides selected from the group consisting of 99m-Technetium, 111-Indium, 117m-Tin, 153-Samarium, 186-Rhenium, 188-Rhenium, 123-Iodine, 125-Iodine, 131-Iodine and 211-Astatine.

15. The bisphosphonic acid derivative labeled with a radioactive nuclide according to any one of claims 1 to 3 or claims 7 to 11, wherein the radioactive nuclide is any one of nuclides selected from the group consisting of 99m-Technetium, 186-Rhenium and 188-Rhenium.

16. The bisphosphonic acid derivative labeled with a radioactive nuclide according to any one of claim 1, 4, 5 or 6, wherein the radioactive nuclide is any one of nuclides selected from the group consisting of 123-Iodine, 125-Iodine and 131-Iodine.

17. A radioactive agent for diagnosis of the bone disease containing, as the active ingredient, any one of the bisphosphonic acid derivatives labeled with a radioactive nuclide according to claim 12.

18. A radioactive agent for diagnosis of the bone disease containing, as the active ingredient, any one of the bisphosphonic acid derivatives labeled with a radioactive nuclide according to claim 13.

19. A radioactive agent for therapy of the bone disease containing, as the active ingredient, any one of the bisphosphonic acid derivatives labeled with a radioactive nuclide according to claim 12.

20. A radioactive agent for therapy of the bone disease containing, as the active ingredient, any one of the bisphosphonic acid derivatives labeled with a radioactive nuclide according to claim 13.

21. A kit for preparing a compound labeled with a radioactive nuclide comprising bisphosphonic acid derivative according to any one of claims 1 to 11.

22. A method for bone imaging by using the bisphosphonic acid derivative labeled with a radioactive nuclide, having the property of urinary excretion, according to any one of claims 1 to 11.

23. A method for labeling a bisphosphonic acid derivative with a radioactive nuclide by reaction between a bisophosphonic acid derivative according to any one of claims 1 to 11 and a peracid ion of radioactive transition metal in the presence of a non-metallic reducing agent to form a complex.

24. A method for labeling a bisphosphonic acid derivative with a radioactive nuclide by reaction between a bisphosphonic acid derivative and a peracid ion of radioactive transition metal in the presence of a non-metallic reducing agent to form a complex, wherein the bisphosphonic acid derivative is a bisphosphonic acid derivative according to any one of claims 1 to 3 and 7 to 11, and the peracid ion of radioactive transition metal is any one of metals selected from the group consisting of pertechnetate (Tc-99m), perrhenate (Re-186) and perrhenate (Re-188), and the non-metallic reducing agent is any one of agents selected from the group consisting of sodium diphenylphosphinobenzene-3-sulfonate, formamidine-sulfonic acid and glucoheptanoic acid.

* * * * *